US012605064B2

(12) United States Patent
Wang et al.

(10) Patent No.: US 12,605,064 B2
(45) Date of Patent: Apr. 21, 2026

(54) METHOD AND DEVICE FOR GENERATING REFRACTIVE PATTERN, AND COMPUTER-READABLE STORAGE MEDIUM

(71) Applicant: SHENZHEN THONDAR TECHNOLOGY CO., LTD, Shenzhen (CN)

(72) Inventors: Ningli Wang, Shenzhen (CN); Xuechuan Dong, Shenzhen (CN); Yequan Huang, Shenzhen (CN); Yan Cui, Shenzhen (CN); Jingyun Guo, Shenzhen (CN)

(73) Assignee: SHENZHEN THONDAR TECHNOLOGY CO., LTD, Shenzhen (CN)

( * ) Notice: Subject to any disclaimer, the term of this patent is extended or adjusted under 35 U.S.C. 154(b) by 786 days.

(21) Appl. No.: 17/717,289

(22) Filed: Apr. 11, 2022

(65) Prior Publication Data

US 2022/0233070 A1 Jul. 28, 2022

Related U.S. Application Data

(63) Continuation of application No. PCT/CN2020/083552, filed on Apr. 7, 2020.

(30) Foreign Application Priority Data

Mar. 16, 2020 (CN) .......................... 202010185058.3

(51) Int. Cl.
*A61B 3/103* (2006.01)
*A61B 3/12* (2006.01)
*A61B 3/14* (2006.01)

(52) U.S. Cl.
CPC ................ *A61B 3/103* (2013.01); *A61B 3/12* (2013.01); *A61B 3/14* (2013.01)

(58) Field of Classification Search
CPC .. A61B 3/103; A61B 3/12; A61B 3/14; A61B 3/028
(Continued)

(56) References Cited

U.S. PATENT DOCUMENTS

2004/0223118 A1 11/2004 Jean et al.
2005/0270488 A1 12/2005 Hanebuchi
(Continued)

FOREIGN PATENT DOCUMENTS

CN 1192132 A 9/1998
CN 101203795 A 6/2008
(Continued)

OTHER PUBLICATIONS

CN 109512380, Method Based On Wavefront Sensing Technique Making Full Retinal Topography; Lin et al.—Machine Translation (Year: 2019).*
(Continued)

*Primary Examiner* — Bumsuk Won
*Assistant Examiner* — Rahman Abdur
(74) *Attorney, Agent, or Firm* — Westbridge IP LLC

(57) ABSTRACT

Disclosed are a method and a device for generating a refractive pattern, and a computer-readable storage medium. The method includes: capturing fundus images of a human eye to be measured, and obtaining refractive information corresponding to the fundus images; calculating resolutions of the fundus images, and generating a resolution sequence of the fundus images according to the resolutions; confirming target resolutions in the resolution sequence, and obtaining the refractive information of fundus images corresponding to the target resolutions; and generating a refractive (Continued)

matrix according to the refractive information, and generating the refractive pattern according to the refractive matrix.

10 Claims, 5 Drawing Sheets

(58) Field of Classification Search
USPC ........................................................ 351/211
See application file for complete search history.

(56) References Cited

U.S. PATENT DOCUMENTS

| | | | |
|---|---|---|---|
| 2008/0079899 A1 | 4/2008 | Fujieda | |
| 2014/0111772 A1* | 4/2014 | Ikegami | A61B 3/1035 |
| | | | 351/211 |
| 2015/0374233 A1 | 12/2015 | Zhang et al. | |
| 2017/0076137 A1 | 3/2017 | Gordley | |
| 2017/0167848 A1* | 6/2017 | Kobayashi | G01B 9/02058 |

FOREIGN PATENT DOCUMENTS

| | | | |
|---|---|---|---|
| CN | 105496351 | A | 4/2016 |
| CN | 108567405 | A | 9/2018 |
| CN | 109512380 | A | 3/2019 |
| CN | 109645956 | A | 4/2019 |
| CN | 110022756 | A | 7/2019 |
| CN | 110461213 | A | 11/2019 |
| CN | 110575134 | A | 12/2019 |
| EP | 1060703 | A2 | 12/2000 |
| JP | 2009000354 | A | 1/2009 |
| JP | 2015226729 | A | 12/2015 |
| WO | 2014169148 | A1 | 10/2014 |
| WO | 2016190392 | A1 | 12/2016 |

OTHER PUBLICATIONS

First Office Action issued in counterpart Chinese Patent Application No. 202010185058.3, dated Nov. 3, 2020.
International Search Report and Written Opinion issued in corresponding PCT Application No. PCT/CN2020/083552, dated Nov. 27, 2020.
First Office Action issued in counterpart Chinese Patent Application No. 202080069140.8, dated Jan. 4, 2023.

* cited by examiner

METHOD AND DEVICE FOR GENERATING REFRACTIVE PATTERN, AND COMPUTER-READABLE STORAGE MEDIUM

CROSS-REFERENCE TO RELATED APPLICATIONS

This application is a continuation application of International Application No. PCT/CN2020/083552, filed on Apr. 7, 2020, which claims priority to Chinese Patent Application No. 202010185058.3, filed on Mar. 16, 2020. The disclosures of the above-mentioned applications are incorporated herein by reference in their entireties.

TECHNICAL FIELD

The present disclosure relates to the technical field of refractive pattern generation, and in particular, to a method and a device for generating a refractive pattern, and a computer-readable storage medium.

BACKGROUND

With the increasing demand for myopia prevention and control in adolescents, a method for measuring a diopter of a peripheral retina is proposed. General refractometer only measures the diopter of the macular area of the human eye, and a refractive topographer can measure the diopter of the fundus area with the large field of view of the human eye. In the previous traditional method, an ophthalmoscope is used, and the refractive information of fundus with large field of view is obtained by artificially refracting different viewing angles of the human eye. This method is time-consuming and labor-intensive, and can only obtain the refractive distribution of the fundus in the horizontal and vertical directions, which cannot meet the technical requirements of existing human eye detection.

The foregoing description is to provide general background information and does not necessarily constitute the prior art.

SUMMARY

The main objective of the present disclosure is to provide a method and a device for generating a refractive pattern, and a computer-readable storage medium, aiming to solve the technical problem that in the related art, using an ophthalmoscope to obtain the refractive information of fundus with large field of view by artificially refracting different viewing angles of the human eye is time-consuming and labor-intensive, which can only obtain the refractive distribution of the fundus in the horizontal and vertical directions, and cannot meet the detection requirement.

In order to achieve the above objective, the present disclosure provides a method for generating a refractive pattern, including the following operations:

capturing fundus images of a human eye to be measured, and obtaining refractive information corresponding to the fundus images;

calculating resolutions of the fundus images, and generating a resolution sequence of the fundus images according to the resolutions;

confirming target resolutions in the resolution sequence, and obtaining the refractive information of fundus images corresponding to the target resolutions; and generating a refractive matrix according to the refractive information, and generating the refractive pattern according to the refractive matrix.

In an embodiment, before the operation of capturing fundus images of a human eye to be measured, and obtaining refractive information corresponding to the fundus images, the method further includes:

obtaining a preset relative position of a focusing optical module; and setting a refractive scanning range of capturing fundus images according to the relative position.

In an embodiment, the operation of calculating resolutions of the fundus images, and generating a resolution sequence of the fundus images according to the resolution includes:

confirming a target position point for calculating the resolutions of the fundus images; and calculating the resolutions of the fundus images according to the target position point.

In an embodiment, the operation of calculating the resolutions of the fundus images according to the target position point includes:

demarcating a preset neighborhood range with the target position point as a center; and calculating the resolutions of the fundus images according to the preset neighborhood range.

In an embodiment, the operation of confirming the target resolutions in the generated resolution sequence, and obtaining a refractive compensation value of the fundus image corresponding to the target resolution include:

confirming outliers in the resolution sequence; and culling the outliers in the resolution sequence, and confirming the target resolution according to the resolution sequence with the outliers being culled.

In an embodiment, the operation of confirming outliers in the resolution sequence includes:

comparing a resolution in the resolution sequence with a preset resolution threshold; and determining that the resolution is an outlier when the resolution is less than or equal to the preset resolution threshold.

In an embodiment, after the operation of comparing a resolution in the resolution sequence with a preset resolution threshold, the method further includes:

determining that the resolution is a non-outlier when the resolution is greater than the preset resolution threshold.

In an embodiment, the operation of confirming the target resolutions in the generated resolution sequence, and obtaining a refractive compensation value of the fundus image corresponding to the target resolution include:

fitting the resolution sequence, and confirming the target resolution according to a fitting result.

In an embodiment, the target resolution is a maximum resolution.

In an embodiment, before the operation of capturing fundus images of a human eye to be measured, and obtaining refractive information corresponding to the fundus images, the method further includes:

obtaining a refractive value of the human eye to be measured; and setting a capturing threshold range of the fundus images based on the refractive value.

In an embodiment, the operation of generating a refractive matrix according to the refractive information, and generating the refractive pattern according to the refractive matrix includes:

writing the refractive information into a preset matrix with a preset format, and generating the refractive matrix according to the preset matrix in which the refractive information is written.

In an embodiment, the operation of generating a refractive matrix according to the refractive information, and generating the refractive pattern according to the refractive matrix includes:

confirming a type of the refractive pattern, and determining a generation format according to the type of the refractive pattern; and generating the refractive pattern corresponding to the refractive matrix according to the generation format.

In an embodiment, the type of the refractive pattern includes point map, block map, stereo map, statistical map, simulated visual map, naked eye defocus curve and simulated curve when wearing lenses.

Besides, in order to achieve the above objective, the present disclosure further provides a device for generating a refractive pattern, including a memory, a processor, and a program for generating a refractive pattern stored on the memory and executed by the processor, when the program for generating the refractive pattern is executed by the processor, the operations of the method for generating the refractive pattern as described above are implemented.

Besides, in order to achieve the above objective, the present disclosure further provides a computer-readable storage medium, a program for generating a refractive pattern is stored on the computer-readable storage medium, and when the program for generating the refractive pattern is executed by a processor, the operations of the method for generating the refractive pattern as described above are implemented.

The embodiments of the present disclosure provides a method for generating a refractive pattern, including: capturing fundus images of a human eye to be measured, and obtaining refractive information corresponding to the fundus images; calculating resolutions of the fundus images, and generating a resolution sequence of the fundus images according to the resolutions; confirming target resolutions in the resolution sequence, and obtaining the refractive information of the fundus images corresponding to the target resolutions; and generating a refractive matrix according to the refractive information, and generating the refractive pattern according to the refractive matrix. In the present disclosure, by constructing a method for calculating a refractive pattern, the target refractive information is determined by the mapping relationship between refractive information and resolution to form a refractive matrix. Thus, the measurement operation of the refractive information of the entire fundus area at one time in a short time is realized, and the measurement efficiency and measurement accuracy are improved.

The realization of the objective, functional characteristics, and advantages of the present disclosure are further described with reference to the accompanying drawings.

DETAILED DESCRIPTION OF THE EMBODIMENTS

It should be understood that the specific embodiments described herein are only used to explain the present disclosure, but not to limit the present disclosure.

The main solution of the embodiments of the present disclosure are: capturing fundus images of a human eye to be measured, and obtaining refractive information corresponding to the fundus image; calculating resolutions of the fundus images, and generating a resolution sequence of the fundus images according to the resolutions; confirming target resolutions in the resolution sequence, and obtaining the refractive information of the fundus images corresponding to the target resolutions; and generating a refractive matrix according to the refractive information, and generating the refractive pattern according to the refractive matrix.

Since in the related art, using an ophthalmoscope to obtain the refractive information of the fundus with a large field of view by manually refracting different viewing angles of the human eye is extremely time-consuming and labor-intensive. It can only obtain the refractive distribution of the fundus in the horizontal and vertical directions, which cannot meet the technical problem of detection requirements.

The present disclosure provides a solution, by constructing a method for calculating a refractive pattern, the target refractive information is determined by the mapping relationship between refractive information and resolution to form a refractive matrix. Thus, the measurement operation of the refractive information of the entire fundus area at one time in a short time is realized, and the measurement efficiency and measurement accuracy are improved.

Figure 1:
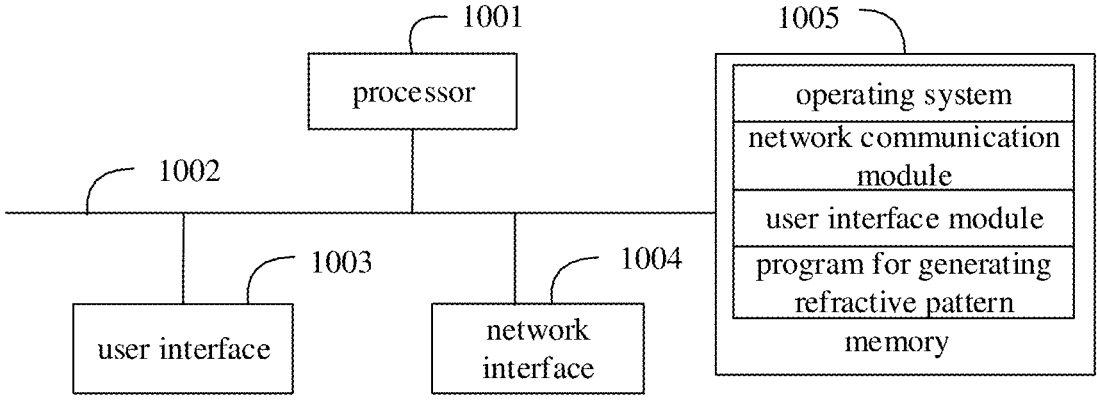
FIG. 1 is a schematic structural diagram of a terminal in a hardware operating environment according to an embodiment of the present disclosure.

As shown in FIG. 1, FIG. 1 is a schematic structural diagram of a terminal in a hardware operating environment according to an embodiment of the present disclosure.

The terminal in the embodiment of the present disclosure can be a portable or non-movable terminal device such as a PC, a smart phone, a tablet computer, an e-book reader, and a portable computer.

As shown in FIG. 1, the terminal can include a processor 1001, such as a CPU, a network interface 1004, a user interface 1003, a memory 1005, and a communication bus 1002. The communication bus 1002 is configured to implement communication between the components. The user interface 1003 can include a display, an input unit such as a keyboard. The user interface 1003 can also include a standard wired interface and a wireless interface. The network interface 1004 can further include a standard wired interface and a wireless interface (such as a WI-FI interface). The memory 1005 can be a high-speed random access memory (RAM) or a non-volatile memory, such as a magnetic disk memory. The memory 1005 can also be a storage device independent of the foregoing processor 1001.

Those skilled in the art should understand that the terminal structure shown in FIG. 1 does not constitute a limitation on the terminal, and can include more or fewer components, a combination of some components, or differently arranged components than shown in the figure.

As shown in FIG. 1, the memory 1005 as a computer storage medium can include an operating system, a network communication module, a user interface module, and a program for generating a refractive pattern.

In the terminal shown in FIG. 1, the network interface 1004 is mainly configured to connect to a background server and perform data communication with the background server. The user interface 1003 is mainly configured to connect to a client (user) and perform data communication with the client. The processor 1001 can be configured to call the program for generating the refractive pattern stored on the memory 1005, and perform the following operations:

capturing fundus images of a human eye to be measured, and obtaining refractive information corresponding to the fundus image;

calculating resolutions of the fundus images, and generating a resolution sequence of the fundus images according to the resolutions;

confirming target resolutions in the resolution sequence, and obtaining the refractive information of the fundus images corresponding to the target resolutions; and generating a refractive matrix according to the refractive information, and generating the refractive pattern according to the refractive matrix.

Further, the processor 1001 can call the program for generating the refractive pattern stored on the memory 1005, and perform the following operations:

obtaining a preset relative position of a focusing optical module; and setting a refractive scanning range of capturing fundus images according to the relative position.

Further, the processor 1001 can call the program for generating the refractive pattern stored on the memory 1005, and perform the following operations:

confirming a target position point for calculating the resolutions of the fundus images; and calculating the resolutions of the fundus images according to the target position point.

Further, the processor 1001 can call the program for generating the refractive pattern stored on the memory 1005, and perform the following operations:

demarcating a preset neighborhood range with the target position point as a center; and calculating the resolutions of the fundus images according to the preset neighborhood range.

Further, the processor 1001 can call the program for generating the refractive pattern stored on the memory 1005, and perform the following operations:

confirming outliers in the resolution sequence; and culling the outliers in the resolution sequence, and confirming the target resolution according to the resolution sequence with the outliers being culled.

Further, the processor 1001 can call the program for generating the refractive pattern stored on the memory 1005, and perform the following operations:

comparing a resolution in the resolution sequence with a preset resolution threshold; and determining that the resolution is an outlier when the resolution is less than or equal to the preset resolution threshold.

Further, the processor 1001 can call the program for generating the refractive pattern stored on the memory 1005, and perform the following operations:

determining that the resolution is a non-outlier when the resolution is greater than the preset resolution threshold.

Further, when the program for generating the refractive pattern is executed by the processor, the following operations are implemented:

fitting the resolution sequence, and confirming the target resolution according to a fitting result.

Further, the processor 1001 can call the program for generating the refractive pattern stored on the memory 1005, and perform the following operations:

defining the target resolution as a maximum resolution.

Further, when the program for generating the refractive pattern is executed by the processor, the following operations are implemented:

obtaining a refractive value of the human eye to be measured; and setting a capturing threshold range of the fundus images based on the refractive value.

Further, the processor 1001 can call the program for generating the refractive pattern stored on the memory 1005, and perform the following operations:

writing the refractive information into a preset matrix with a preset format, and generating the refractive matrix according to the preset matrix in which the refractive information is written.

Further, the processor 1001 can call the program for generating the refractive pattern stored on the memory 1005, and perform the following operations:

confirming a type of the refractive pattern, and determining a generation format according to the type of the refractive pattern; and generating the refractive pattern corresponding to the refractive matrix according to the generation format.

Further, the processor 1001 can call the program for generating the refractive pattern stored on the memory 1005, and perform the following operations:

the type of the refractive pattern includes point map, block map, stereo map, statistical map, simulated visual map, naked eye defocus curve and simulated curve when wearing lenses.

Figure 2:
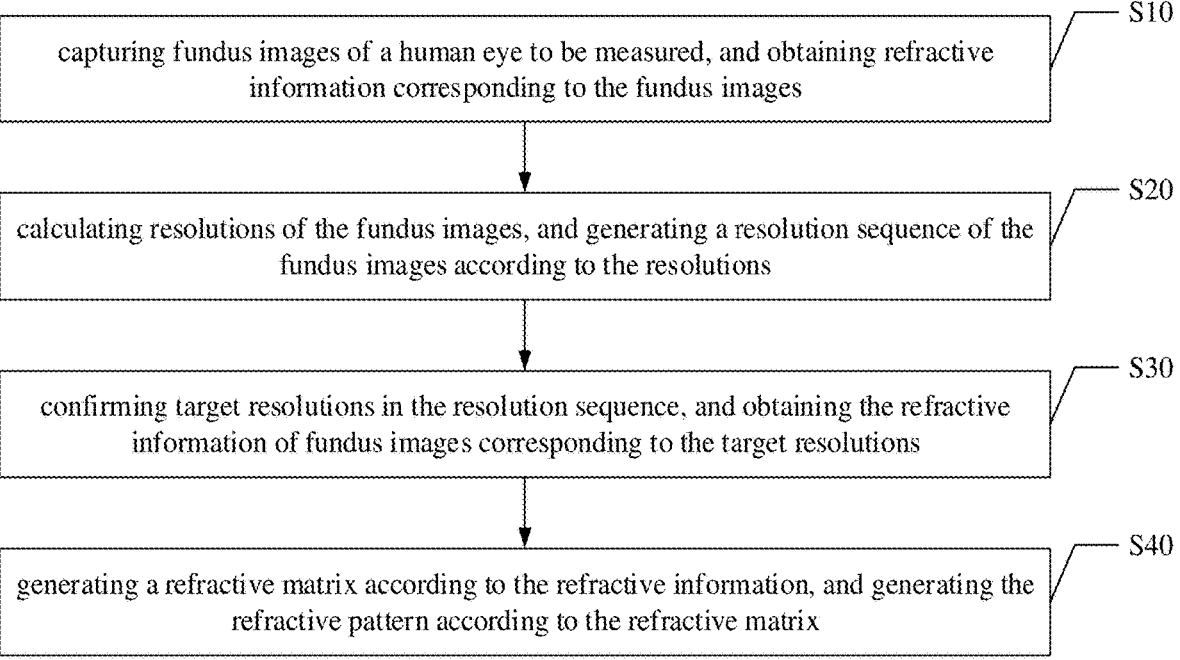
FIG. 2 is a schematic flowchart of a method for generating a refractive pattern according to a first embodiment of the present disclosure.

As shown in FIG. 2, FIG. 2 is a schematic flowchart of a method for generating a refractive pattern according to a first embodiment of the present disclosure. The method for generating the refractive pattern is applied to a refractive topographer, and the method for generating a refractive pattern includes the following operations:

Operation S10, capturing fundus images of a human eye to be measured, and obtaining refractive information corresponding to the fundus image.

According to the current requirements for human eye detection, the fundus images of the human eye to be measured are captured. When capturing the fundus images of the human eye currently to be measured, the fundus images can be captured based on a refractive topographer, fundus camera, or other control device connected to the refractive topographer/fundus camera, to obtain refractive information corresponding to the fundus images according to the captured fundus images. In practical applications, when capturing the fundus images, the fundus camera drives the relative position movement of the focusing optical module through the motor, and captures the fundus images after performing refractive adjustment. Further, the moving distance of the focusing optical module corresponds to a certain range of refractive compensation values, that is, the refractive scanning range. The refractive scanning range can be a fixed range or a dynamic range. The definition of the refractive scanning range can be based on the pre-verified refractive information of the patient to be measured, and then the dynamic refractive range corresponding to the fundus image is set based on the refractive information. Before the operation of capturing fundus images of a human eye to be measured, and obtaining refractive information corresponding to the fundus images, the method further includes the following operations:

obtaining a refractive value of the human eye to be measured; and setting a capturing threshold range of the fundus images based on the refractive value.

The refractive value of the human eye to be measured is obtained based on the refractive value detected by the current human eye to be measured, so as to preset the capturing threshold range of the fundus image based on the refractive value, that is, the refractive scanning range. The refractive scanning range can be a fixed range or a dynamic range, so that the fundus camera captures the fundus image according to the preset capturing threshold range, that is, the refractive scanning range. As such, the fundus refractive scanning of the fundus image captured by the focusing optical module is performed with a fixed diopter at equal intervals, or the operation of capturing the fundus image is performed within a certain range with a diopter at unequally intervals. The fundus images include a plurality of images.

Therefore, when the refractive information corresponding to the fundus images is obtained according to the captured fundus image, since the fundus images are captured in a certain refractive scanning range, the refractive information corresponding to the fundus images can be obtained based on the preset refractive scanning range. In this way, the refractive information corresponding to the fundus images is confirmed according to the corresponding specific refractive scan range value when the fundus images are captured.

Operation S20, calculating resolutions of the fundus images, and generating a resolution sequence of the fundus images according to the resolutions.

Figure 3:
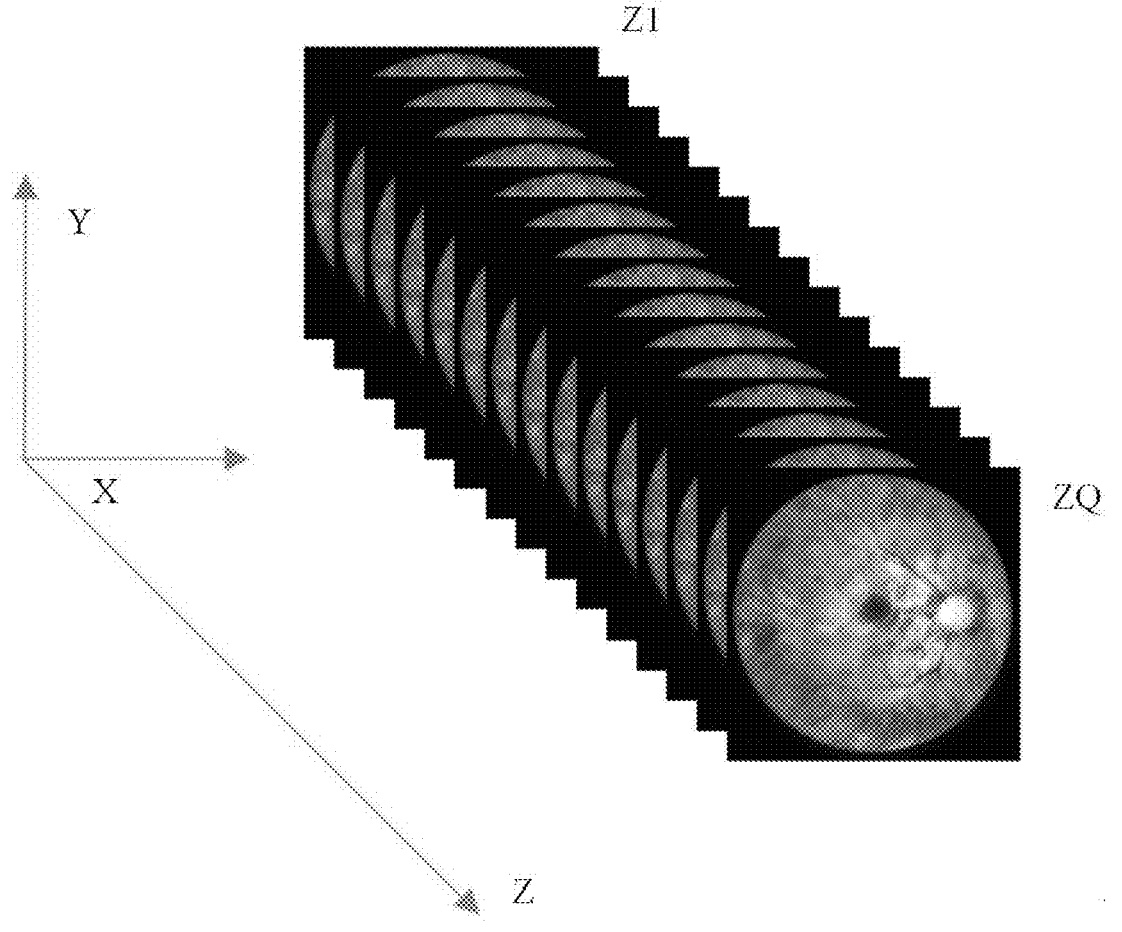
FIG. 3 is a schematic diagram of coordinates of a refractive compensation value.

The resolutions of the fundus images are calculated according to the currently captured fundus images and the refractive information corresponding to the fundus images. When calculating the resolutions of the fundus images, the corresponding calculation method and calculation parameters can be selected according to the capturing device of the current fundus image and the application scene, and the calculation method of the corresponding resolution can be calculated based on the fundus image, such as gradient, grayscale variance or entropy function. Besides, before calculating the fundus image, it is necessary to confirm whether the captured fundus image needs to be registered based on the refractive threshold range of the current fundus image and the capturing time. If the refractive scan process corresponding to the currently defined refractive threshold range takes less time, and the captured fundus image has a small change in magnification relative to the fundus, the image registration operation of the fundus image may not be performed, and the determination of the registration operation may be performed based on the currently set registration preset time. The fundus image obtained based on the refractive information and the relevant technical content of calculating the resolution based on the fundus image all belong to the protection scope of the present disclosure. In this way, according to the calculated resolution of the fundus image, in the case of multiple fundus images, the numerical value of the resolution is also multiple. According to the calculated resolution value, a resolution sequence based on the fundus image is generated. Further, when the resolution sequence includes a plurality of resolution values, the arrangement order of the resolution sequence can be based on the change of the refractive compensation value of the refractive threshold range in which the fundus image is currently captured. There may be differences in the arrangement order under different coordinates. The coordinate directions include X, Y, and Z directions, all of which correspond to different refractive compensation values. The coordinate definition information may be shown in FIG. 3, and FIG. 3 is a schematic diagram of coordinates of the refractive compensation value.

When calculating the resolutions of the fundus images, the resolutions can be calculated based on the way of defining clear points. The operation of calculating resolutions of the fundus images, and generating a resolution sequence of the fundus images according to the resolutions includes the following operations:

confirming a target position point for calculating the resolutions of the fundus images; and calculating the resolutions of the fundus images according to the target position point.

According to the currently captured fundus image, when calculating the resolutions of the fundus images, it is necessary to confirm the target position point for calculating the resolutions of the fundus images. When confirming that the target position point is the fulcrum, the dimension of the captured fundus image is M×N, and the target position point for calculating the resolution is selected based on the matrix of the M×N dimension, the method for selecting the target position point can be as follows:

a. All M×N points are used as target position points;

b. The position point is selected according to a constant number of intervals, for example, a target position point is selected every 10 horizontally and vertically;

c. Several points at non-equidistant intervals in the two-dimensional matrix are selected as the target position points.

As described above, since the fundus image is based on a matrix of M×N dimension, each selected position point has coordinates corresponding to the M×N matrix. The coordinates of the target location point can be defined as (x, y). As such, according to the target position point of the currently confirmed fundus image, when there are a plurality of fundus images, from the 1st to the Qth fundus image, the resolution of each fundus image based on the selected target position is calculated sequentially. The qth (q=1, 2, . . . , Q) image is Iq, and the resolution of the image based on the target position point (x, y) is calculated sequentially. The resolution adopts calculation methods in the field of image processing, such as gradient, grayscale variance, entropy function, or the like, and appropriate calculation methods and calculation parameters can be selected according to specific devices and application scenarios.

Since the data of the fundus image is too large, considering the efficiency of the resolution calculation, the resolution calculation range can be demarcated based on the confirmed target position points to improve the resolution calculation efficiency. The operation of calculating the resolutions of the fundus images according to the target position point includes the following operations:

demarcating a preset neighborhood range with the target position point as a center; and calculating the resolutions of the fundus images according to the preset neighborhood range.

Figure 4:
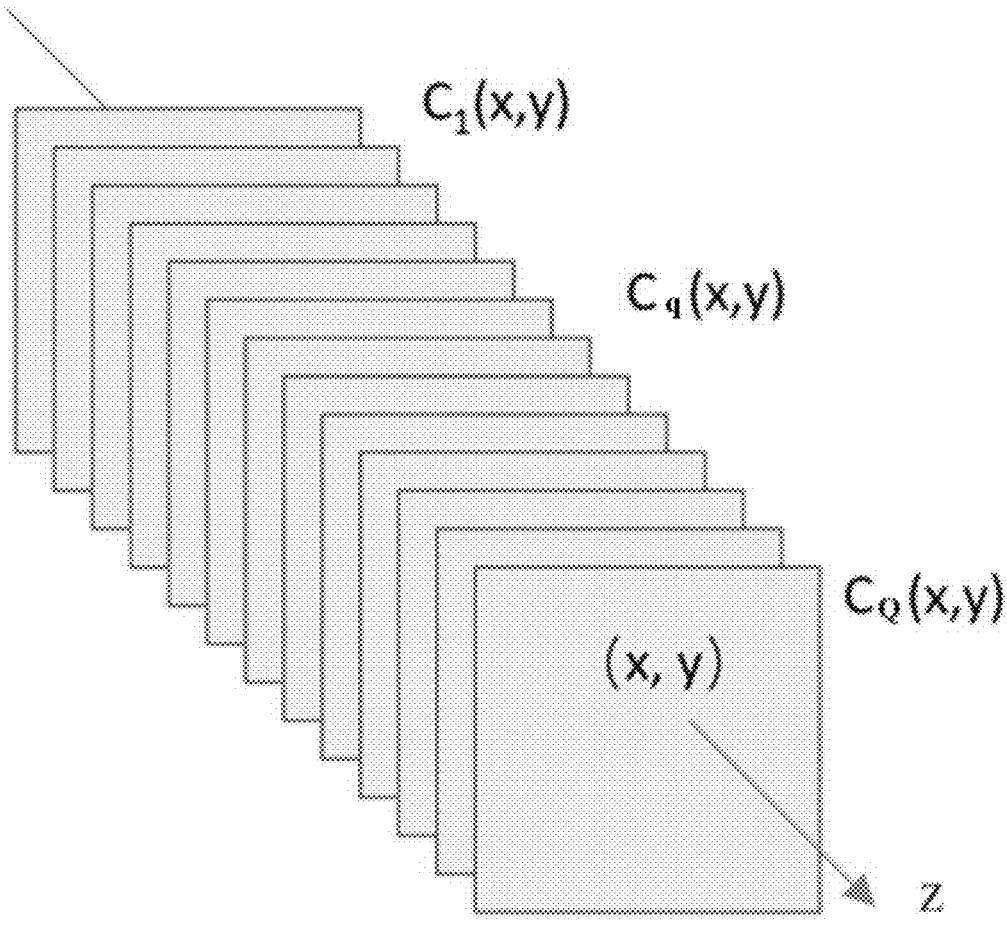
FIG. 4 is a schematic diagram of a resolution based on a target position point.

According to the currently determined target position point (x, y) based on each fundus image, a suitable neighborhood range is selected with the target position point as the center, and the resolution within the neighborhood range is calculated. In this way, the resolution of the target position point is denoted as Cq(x, y), and the confirmation method based on the resolution within the neighborhood range can be shown in FIG. 4, and FIG. 4 is a schematic diagram of the resolution based on the target position point.

Operation S30, confirming target resolutions in the resolution sequence, and obtaining the refractive information of the fundus images corresponding to the target resolutions.

Figure 5:
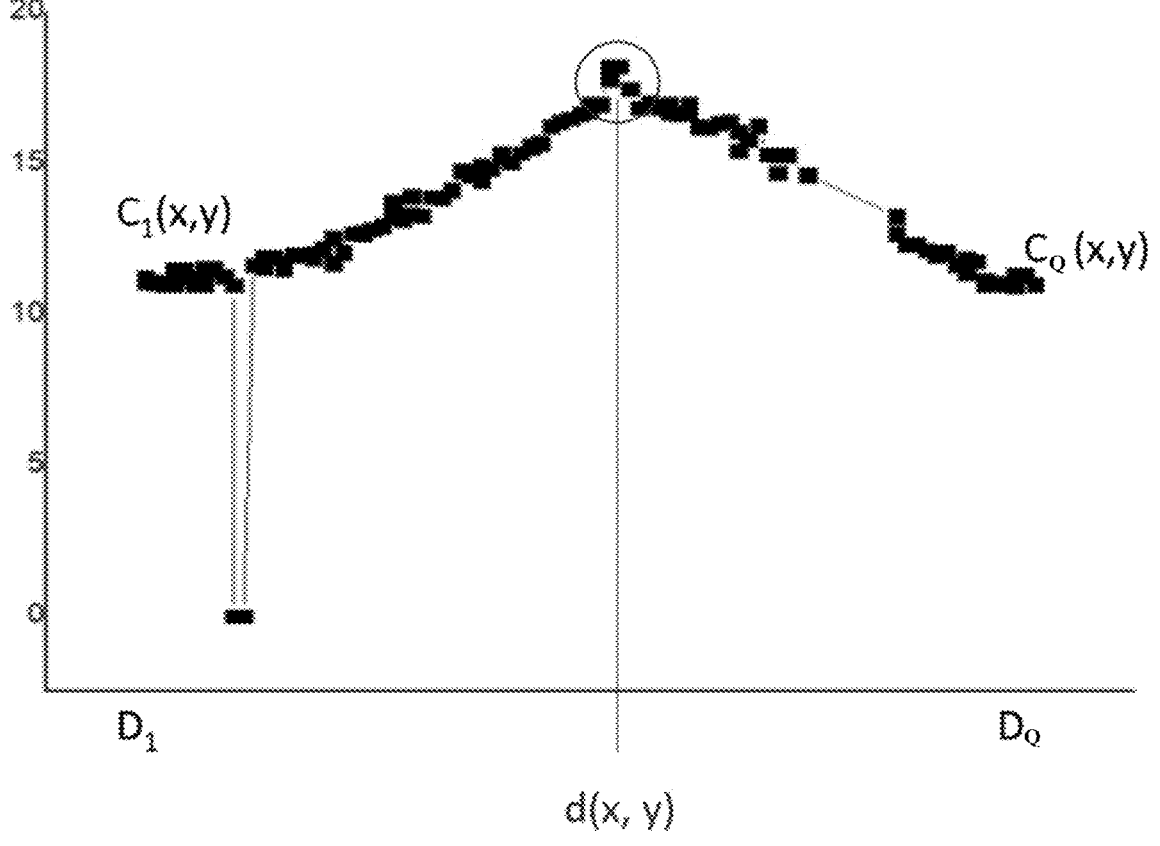
FIG. 5 is a schematic diagram of confirming the target resolution in the resolution sequence.

According to the fundus image whose resolution has been currently calculated, the resolution sequence formed by the resolution is used to confirm the optimal resolution in the resolution sequence. The optimal resolution can be defined as the maximum resolution or the best resolution, etc., and can be defined as the target resolution. As such, in the currently captured Q fundus images, the resolution calculated at the target position point (x, y) is different. Under the condition that the current fundus image has the corresponding refractive information, there will be an optimal resolution, that is, the target resolution. The calculation method of the target resolution can confirm the maximum value of the resolution of the target position point in the Q fundus images, which is defined as the target resolution. Further, since there are multiple resolution sequences in different directions, there are also multiple target resolutions defined based on the optimal resolution, that is, the target resolution is multiple. The confirmation method of the target resolution can be shown in FIG. 5, and FIG. 5 is a schematic diagram of confirming the target resolution in the resolution sequence. Besides, since the captured fundus image will be affected by many factors such as optical noise, electronic noise and software processing during capturing, some disturbance will occur. A fitting operation can be performed based on the resolution sequence, and the target resolution is confirmed from the resolution sequence according to the fitting result. The operation of confirming the target resolution in the generated resolution sequence, and obtaining the refractive compensation value of the fundus image corresponding to the target resolution includes:

> identifying outliers in the resolution sequence; and
> culling the outliers in the resolution sequence, and confirming the target resolution according to the resolution sequence with the outliers being culled.

During the refractive scanning process, the patient blinks, the eyelid pull-down and other phenomena will cause the resolution of some fundus images to deviate significantly from the resolution trend of the entire fundus image. As such, considering the resolution value of the entire fundus image, the resolution sequence is generated based on the current resolution, it is necessary to cull outliers in the resolution sequence. Alternatively, when the resolution in the resolution sequence is mostly abnormal, that is, when multiple resolution values are outliers, only part of the resolution data in the resolution sequence can be selected to form a new resolution sequence, and then the target resolution can be confirmed through the generated new resolution sequence.

As described above, the operation of identifying outliers in the resolution sequence includes:

> comparing a resolution in the resolution sequence with a preset resolution threshold; and
> determining that the resolution is an outlier when the resolution is less than or equal to the preset resolution threshold.

The operation for confirming the outlier in the resolution sequence can be performed by comparing each resolution value in the resolution sequence with a preset value. That is, when the resolution is greater than the preset value, it is determined that the resolution value is not abnormal. When the mean value of the resolution is smaller than the preset value, it is determined that the resolution value is an outlier, and the resolution is eliminated from the resolution sequence. According to the above-mentioned operation of culling outliers in the resolution sequence, the resolution sequence with outliers being culled is defined as a vector Q', and a polynomial function is used to fit the vector Q'. The target resolution in the resolution sequence is confirmed according to the fitting result. That is, the maximum value of the resolution is Gmax, a number of the corresponding fundus image when the resolution is the largest is defined as nmax, and the refractive compensation value of the target position point corresponding to the resolution is defined as Dx, y. $Dx,y=(nmax-30)*0.1$.

As such, after the target resolution is confirmed by the resolution sequence, it is confirmed that the target resolution corresponds to the refractive information of the fundus image. That is, the refractive information is the refractive information of the fundus image corresponding to the target resolution when capturing. Besides, the refractive information can also be defined as refractive compensation value, which can be defined as a numerical value processed by inversion, linear transformation, or some other function. Further, the refractive information can also be defined as fundus data based on fundus images, such as visual acuity value, refractive value, or the like. The technical contents of the image application data of the fundus image confirmed by the resolution of the fundus image all belong to the protection scope of the present disclosure.

Operation S40, generating a refractive matrix according to the refractive information, and generating the refractive pattern according to the refractive matrix.

The refractive matrix is generated according to the refractive information. During the process of generating the refractive matrix, the refractive matrix can be formed by writing the refractive information based on a preset matrix format. The operation of generating the refractive matrix according to the refractive information, and generating the refractive pattern according to the refractive matrix includes:

> writing the refractive information into a preset matrix with a preset format, and generating the refractive matrix according to the preset matrix in which the refractive information is written.

According to the obtained refractive information, the refractive information is written into the preset matrix with the preset format. The matrix is defined as a set of complex numbers or real numbers arranged in a rectangular array, and is a square matrix formed by coefficients and constants from a system of equations. Based on the preset matrix disclosed in this embodiment, the preset matrix formed after deformation needs to be defined based on the existing matrix, and the deformation operation can be set by the relevant technical personnel to write the refractive information.

Further, based on specific clinical application requirements, the refractive matrix can perform secondary numerical operations and be displayed graphically. Typical applications of numerical operations are as follows.

Based on the refractive information matrix, the refractive compensation value matrix is obtained from the refractive information, and the inversion operation is performed. The absolute refractive value of each position point is obtained to study the change of peripheral refraction compared with the central refraction. The mean value of the central refraction can be calculated first, and then the mean value can be subtracted from the entire refractive matrix, that is, the change in the periphery refraction compared with the center refraction can be obtained. The refractive information with D as the unit is converted to the value with the lens degree as the unit, to confirm the topographic map type of the current refractive topographer. The topographic map types include point map, block map, stereo map, statistical map and simulated visual map. In this way, according to the confirmed topographic map type, the operation of generating a refractive topographic map based on the image and the corresponding refractive compensation value map is performed. In practical applications, there are differences in the representation of different topographic map types, and the specific contents can be as follows.

The point map (fov-raw) provides 10°, 20°, 30°, 40° field of view and a difference between the refractive value corresponding to each site and the refractive value of the macular position.

The block map (grid-mean) divides the point map into 8*8 blocks on average, and the numerical value represents the average value of the diopter in each block.

The stereo map (3d-color) converts the point refractive value to 3D shape. The XY direction of the 3D map is the same as the previous two maps, the abscissa is the temporal-Nasal of the right eye and the left eye (Nasal-Temporal), and the ordinate is Inferior-Superior. The value of each point represents the defocus value of the current position, that is, the diopter difference with the macula. The diopter value at the macula is taken as the 0 reference, and the diopter difference is taken between other positions and the macula. "+" indicates that the diopter is larger than that at the macular position, and "−" indicates that the diopter is smaller than that at the macular position.

The statistical map (statistics) calculates the calculation parameters of different fundus regions according to the data of refractive topography as shown in FIG. 4. TRDV is the average defocus value of the total area, which represents the average deviation of the curved surface from the horizontal plane in the stereogram. RDV-15, RDV-30, RDV-45 represent the average defocus values in different ranges from the macula. RDV-S, RDV-N, RDV-I, RDV-T represent the average defocus values in different quadrants of superior, nasal, inferior and temporal.

The simulated visual map (visual) simulates the resolution of the actual scene at different positions of the eyes according to the refractive topographic map data. It is considered that the position of the macula is clear. The absolute difference between each position and the macula is used as a benchmark of resolution. The larger the absolute difference, the blurrier, and the smaller the absolute difference, the clearer. Here, smooth filtering is used to achieve this local blurring operation. The filter coefficient of each position is related to its corresponding absolute difference. The larger the absolute difference, the larger the filter coefficient.

Naked-eye defocus curve (naked-eye): as shown in FIG. 5, calculate the diopter difference between the 15°, 30°, 45° positions and the macula. If the difference is "+", it is hyperopic defocus, that is, the defocus curve is outside the eyeball. If the difference is "−", it is myopic defocus, and the defocus curve is inside the eyeball.

Besides, the simulated graph when wearing the lens is shown below:

Defocus curve when wearing ordinary glass (frame-glass): use the naked eye as a reference to simulate the defocus curve when wearing glasses. Wearing glasses enhances the original degree of defocus, that is, the curvature of the defocus surface becomes smaller, and the deviation is further away from the eyeball surface.

Defocus curve when wearing ok glass (ok-glass): after wearing ok glass, the defocus surface and the eyeball surface return.

In this embodiment, by constructing a method for calculating a refractive pattern, the target refractive information is determined by the mapping relationship between refractive information and resolution to form a refractive matrix. Thus, the measurement operation of the refractive information of the entire fundus area at one time in a short time is realized, and the measurement efficiency and measurement accuracy are improved.

Besides, the embodiments of the present disclosure further provide a computer-readable storage medium. A program for generating a refractive pattern is stored on the computer-readable storage medium. When the program for generating the refractive pattern is executed by a processor, the following operations are implemented:

capturing fundus images of a human eye to be measured, and obtaining refractive information corresponding to the fundus images;

calculating resolutions of the fundus images, and generating a resolution sequence of the fundus images according to the resolutions;

confirming target resolutions in the resolution sequence, and obtaining the refractive information of the fundus images corresponding to the target resolutions; and generating a refractive matrix according to the refractive information, and generating the refractive pattern according to the refractive matrix.

Further, when the program for generating the refractive pattern is executed by the processor, the following operations are implemented:

obtaining a preset relative position of a focusing optical module; and setting a refractive scanning range of capturing fundus images according to the relative position.

Further, when the program for generating the refractive pattern is executed by the processor, the following operations are implemented:

confirming a target position point for calculating the resolutions of the fundus images; and calculating the resolutions of the fundus images according to the target position point.

Further, when the program for generating the refractive pattern is executed by the processor, the following operations are implemented:

demarcating a preset neighborhood range with the target position point as a center; and calculating the resolutions of the fundus images according to the preset neighborhood range.

Further, when the program for generating the refractive pattern is executed by the processor, the following operations are implemented:

confirming outliers in the resolution sequence; and culling the outliers in the resolution sequence, and confirming the target resolution according to the resolution sequence with the outliers being culled.

Further, when the program for generating the refractive pattern is executed by the processor, the following operations are implemented:

comparing a resolution in the resolution sequence with a preset resolution threshold; and determining that the resolution is an outlier when the resolution is less than or equal to the preset resolution threshold.

Further, when the program for generating the refractive pattern is executed by the processor, the following operations are implemented:

determining that the resolution is a non-outlier when the resolution is greater than the preset resolution threshold.

Further, when the program for generating the refractive pattern is executed by the processor, the following operations are implemented:

fitting the resolution sequence, and confirming the target resolution according to a fitting result.

Further, when the program for generating the refractive pattern is executed by the processor, the following operations are implemented:

defining the target resolution as a maximum resolution.

Further, when the program for generating the refractive pattern is executed by the processor, the following operations are implemented:

obtaining a refractive value of the human eye to be measured; and setting a capturing threshold range of the fundus image based on the refractive value.

Further, when the program for generating the refractive pattern is executed by the processor, the following operations are implemented:

writing the refractive information into a preset matrix with a preset format, and generating the refractive matrix according to the preset matrix in which the refractive information is written.

Further, when the program for generating the refractive pattern is executed by the processor, the following operations are implemented:

confirming a type of the refractive pattern, and determining a generation format according to the type of the refractive pattern; and generating the refractive pattern corresponding to the refractive matrix according to the generation format.

Further, when the program for generating the refractive pattern is executed by the processor, the following operations are implemented:

the type of the refractive pattern includes point map, block map, stereo map, statistical map, simulated visual map, naked eye defocus curve and simulated curve when wearing lenses.

It should be noted that in this document, the terms "include", "include" or any other variants thereof are intended to cover a non-exclusive inclusion. Thus, a process, method, article, or system that includes a series of elements not only includes those elements, but also includes other elements that are not explicitly listed, or also includes elements inherent to the process, method, article, or system. If there are no more restrictions, the element defined by the sentence "including a . . . " does not exclude the existence of other identical elements in the process, method, article or system that includes the element.

The serial numbers of the foregoing embodiments of the present disclosure are only for description, and do not represent the advantages and disadvantages of the embodiments.

Through the description of the above embodiment, those skilled in the art can clearly understand that the above-mentioned embodiments can be implemented by software plus a necessary general hardware platform, of course, it can also be implemented by hardware, but in many cases the former is a better implementation. Based on this understanding, the technical solution of the present disclosure can be embodied in the form of software product in essence or the part that contributes to the existing technology. The computer software product is stored on a storage medium (such as ROM/RAM, magnetic disk, optical disk) as described above, including several instructions to cause a terminal device (such as a mobile phone, a computer, a server, an air conditioner, or a network device, etc.) to execute the method described in each embodiment of the present disclosure.

The above are only some embodiments of the present disclosure, and do not limit the scope of the present disclosure thereto. Under the inventive concept of the present disclosure, equivalent structural transformations made according to the description and drawings of the present disclosure, or direct/indirect application in other related technical fields are included in the scope of the present disclosure.

What is claimed is:

1. A method for measuring refractive information, comprising the following operations:

obtaining refractive information corresponding to fundus images; and obtaining refractive information of target position points of a fundus according to the refractive information corresponding to the fundus images;

wherein the operation of obtaining the refractive information of the target positions of the fundus according to the refractive information corresponding to the fundus images comprises:

obtaining a target resolution corresponding to each of the target position points; and confirming the refractive information of the target positions of the fundus according to the target resolution; and wherein before the operation of obtaining the target resolution corresponding to each of the target position points, the method further comprises:

calculating resolutions of the fundus images based on a selected target position point; and determining an optimum resolution according to the resolutions as the target resolution.

2. The method of claim 1, wherein the operation of calculating resolutions of the fundus images based on the selected target position point comprises:

demarcating a preset neighborhood range with the selected target position point as a center; and calculating the resolutions of the fundus images according to the neighborhood range.

3. The method of claim 1, wherein the resolutions form a resolution sequence, and the operation of determining the optimum resolution according to the resolutions comprises:

fitting the resolution sequence, and determining the target resolution according to a fitting result.

4. The method of claim 1, wherein the fundus images are obtained under different refractive adjustment.

5. The method of claim 4, wherein a state of the refractive adjustment is set through refractive scanning.

6. The method of claim 1, wherein the refractive information corresponding to the fundus images is a refractive compensation value, or the refractive information corresponding to the fundus images is obtained by processing a refractive compensation value through a function.

7. The method of claim 6, wherein the fundus images correspond to different refractive compensation values.

8. The method of claim 1, wherein after the operation of obtaining the refractive information of the target position points of the fundus according to the refractive information corresponding to the fundus images, the method further comprises:

generating a refractive topographic map based on the refractive information corresponding to the fundus images.

9. The method of claim 1, wherein after the operation of obtaining the refractive information of the target position points of the fundus according to the refractive information corresponding to the fundus images, the method further comprises:

generating a refractive matrix based on the obtained refractive information, and generating a refractive topographic map according to the refractive matrix.

10. A device for measuring refractive information, comprising a memory, a processor, a program for measuring refractive information stored on the memory and executed by the processor, when the program for measuring the refractive information is executed by the processor, the operations of the method of claim 1 are implemented.

\* \* \* \* \*